United States Patent [19]
Hamm et al.

[11] Patent Number: 5,281,798
[45] Date of Patent: Jan. 25, 1994

[54] METHOD AND SYSTEM FOR SELECTIVE REMOVAL OF MATERIAL COATING FROM A SUBSTRATE USING A FLASHLAMP

[75] Inventors: Richard R. Hamm; John D. Hoogerwerf, both of San Diego, Calif.

[73] Assignee: Maxwell Laboratories, Inc., San Diego, Calif.

[21] Appl. No.: 813,864

[22] Filed: Dec. 24, 1991

[51] Int. Cl.$^5$ .............................. G01J 1/32
[52] U.S. Cl. ................... 250/205; 250/226; 219/121.62
[58] Field of Search .............. 250/205, 226; 219/121.62, 121.61, 121.66, 121.69; 356/32 C, 328

[56] References Cited

U.S. PATENT DOCUMENTS

| | | | |
|---|---|---|---|
| 3,700,850 | 10/1972 | Lumley et al. | 219/121 |
| 3,986,391 | 10/1976 | Vahaviolos | 219/121 |
| 4,114,018 | 9/1978 | Von Allmen et al. | 219/121.62 |
| 4,249,956 | 2/1981 | Hartman | 134/7 |
| 4,398,961 | 8/1983 | Mason | 134/19 |
| 4,419,562 | 12/1983 | Jon et al. | 219/130 |
| 4,491,484 | 1/1985 | Williams | 134/4 |
| 4,504,727 | 3/1985 | Melcher et al. | 219/121 |
| 4,543,486 | 9/1985 | Rose | 250/492 |
| 4,588,885 | 5/1986 | Lovoi et al. | 250/226 |
| 4,682,594 | 7/1987 | Mok | 128/303 |
| 4,718,974 | 1/1988 | Minaee | 156/643 |
| 4,731,125 | 3/1988 | Carr | 134/17 |
| 4,737,628 | 4/1988 | Lovoi | 250/226 |
| 4,803,021 | 2/1989 | Werth et al. | 264/25 |
| 4,836,858 | 6/1989 | Reinhart | 134/1 |
| 4,867,796 | 9/1989 | Asmus et al. | 131/1 |
| 4,994,639 | 2/1991 | Dickinson et al. | 219/121 |
| 5,013,366 | 5/1991 | Jackson et al. | 134/1 |
| 5,024,968 | 6/1991 | Engelsberg | 437/173 |
| 5,026,964 | 6/1991 | Somers et al. | 219/121.62 |

FOREIGN PATENT DOCUMENTS 0391113 3/1990 European Pat. Off. .
3710816 10/1988 Fed. Rep. of Germany .
9013897 11/1990 PCT Int'l Appl. .

OTHER PUBLICATIONS

Klauser, H. E., "Closed-Loop Laser Control System", IBM Technical Disclosure Bulletin, 24(9), Feb. 1882), pp. 4691-4692.

Yaeck, C. E., et al., "Transient Photoacoustic Monitoring of Pulse Laser Drilling", Appl. Phys. Lett., 41(11), (Dec. 1, 1982), pp. 1043-1044.

Schmitz, W. N., "Xenon Flashlamp/$CO_2$ Pellet Blasting or Paint Stripping/Coatings Removal", Proceedings of the DOD/Industry Advanced Coatings Removal Conference, San Diego, Calif. (Apr. 30/May 2, 1991) (no page No.).

Cates, M. C., "Modeling of the Flashblast Coating Removal Process", Proceedings of the DOD/Industry Advanced Coatings Removal Conference, San Diego, Calif. (Apr. 30-May 2, 1991), pp. 1-13.

Primary Examiner—David C. Nelms
Assistant Examiner—Que T. Le
Attorney, Agent, or Firm—Fitch, Even, Tabin & Flannery

[57] ABSTRACT

Pulsed light sources, such as a flashlamp or laser, remove coatings from substrates via the ablation method. A photodetector circuit, sensing reflected light from the surface being ablated, provides a feedback signal that indicates the reflected color intensity of the surface being ablated. The boundary between the coatings or substrate surfaces is distinguished by a change in color intensity between an upper coating and an undercoating, e.g., between a topcoat of paint and a primer coat of paint, or between a coating and the substrate surface itself. The color intensity determination thus provides a measure relative to when one coating has been removed and another coating remains. The photodetector circuit is also useful for providing feedback information relative to the quality of a stripped work surface for quality control or other purposes.

18 Claims, 5 Drawing Sheets

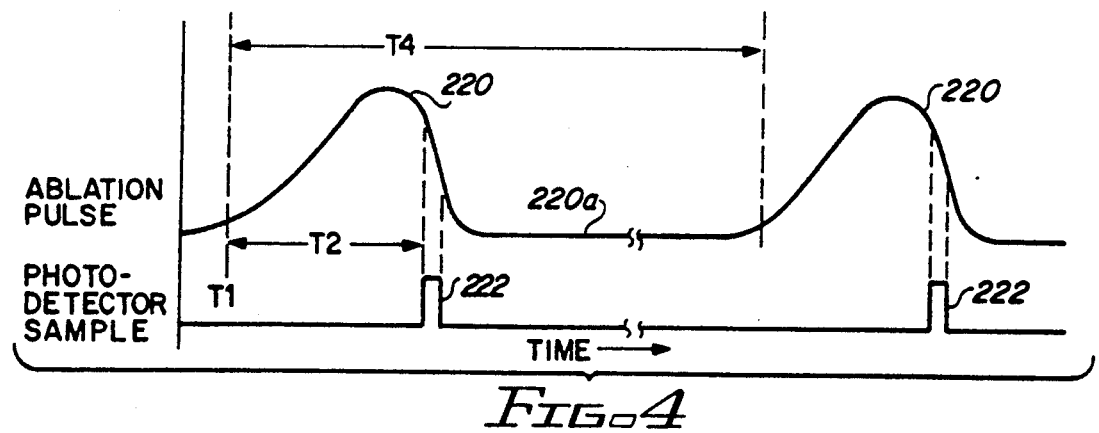
FIG-4
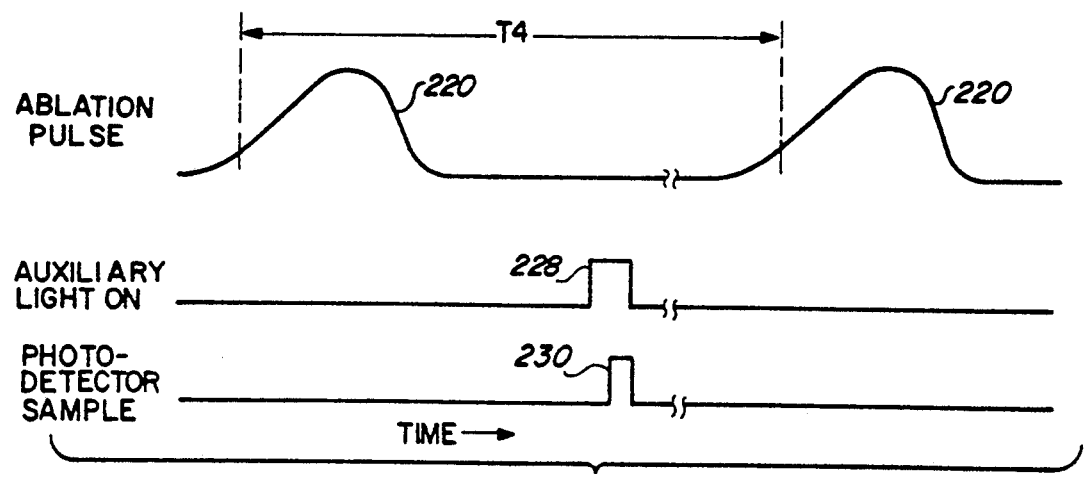
FIG-5
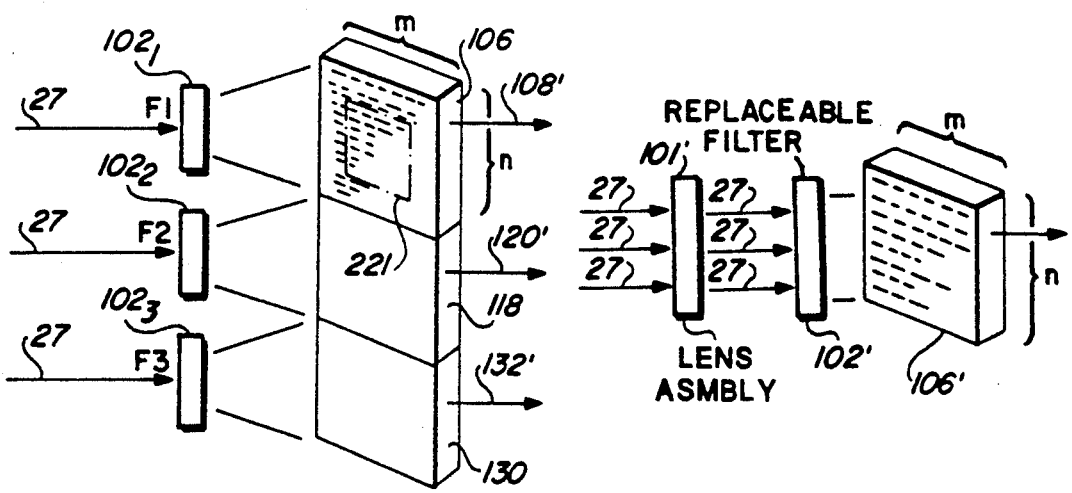
FIG-6
FIG-7

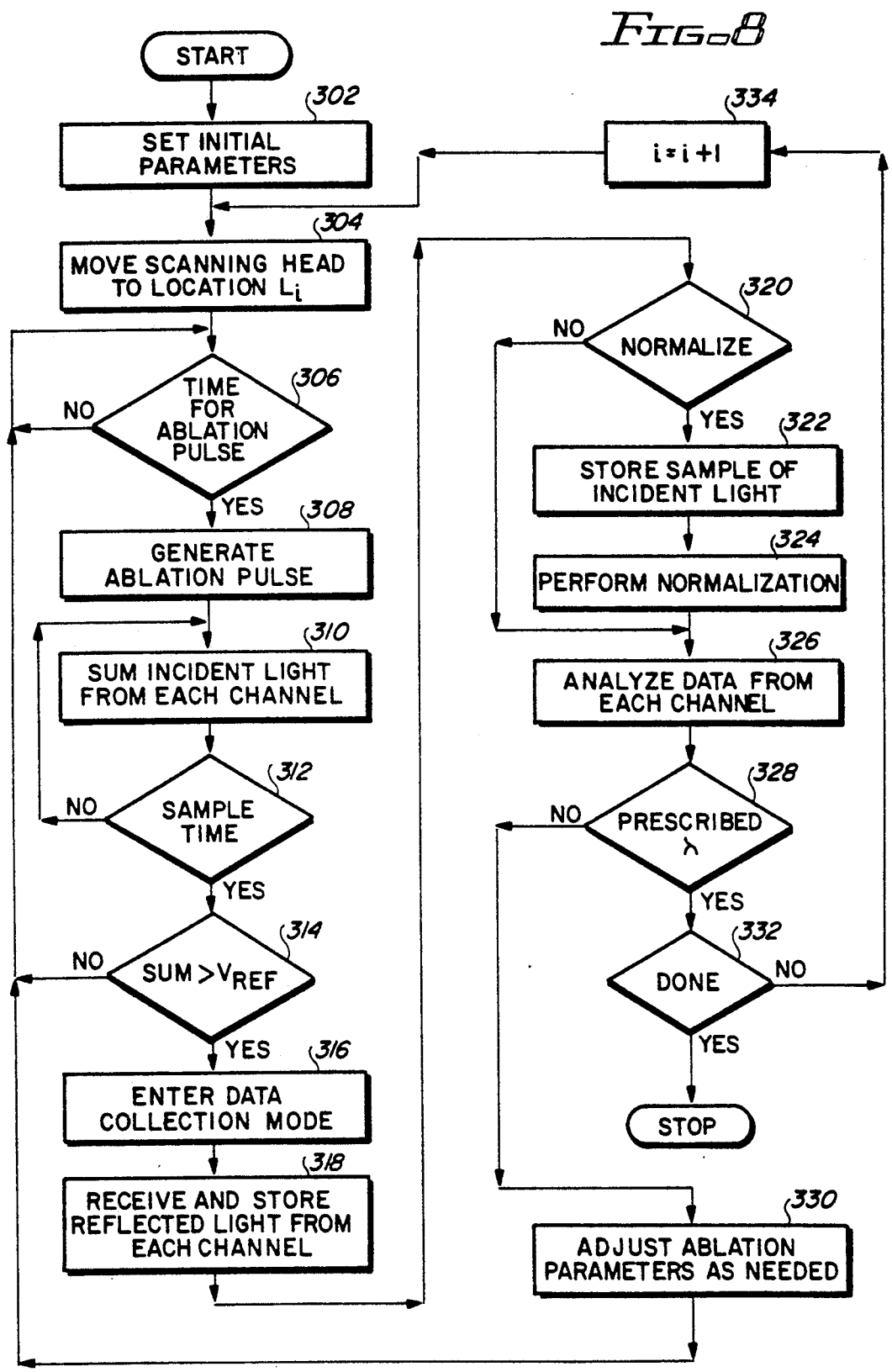

METHOD AND SYSTEM FOR SELECTIVE REMOVAL OF MATERIAL COATING FROM A SUBSTRATE USING A FLASHLAMP

The present invention relates to a material removal process and system, and more particularly, to a material removal process and system that uses pulsed light from a flashlamp, or equivalent pulsed high energy light source (such as a laser), to ablate the material to be removed; and also uses optical feedback from the surface being ablated to determine when the proper amount of material has been removed.

BACKGROUND OF THE INVENTION

Material coatings play an important role in our manufactured products based society. Coatings provide immunity to corrosion, thermal insulation, shielding, as well as appearance enhancement, and an aid in identification.

During the life of many manufactured products, such as bridges, aircraft, automobiles, and ships, painted coatings require removal and replacement for a variety of reasons. For example, refurbishment of the paint on aircraft is a regular maintenance item. Commercial airlines repaint their aircraft about every 4–5 years of service. The United States military typically repaints its aircraft after three years of service, or less. Coatings on the exterior surfaces of large ships or bridges require periodic refurbishment in order to prevent or inhibit corrosion.

The removal of paint from the surfaces of aircraft presents special problems Such surfaces are large, irregularly shaped, and relatively delicate. Because the surfaces of aircraft are typically lightweight aluminum or organically based composite materials, such surfaces and the underlying substrates are particularly susceptible to damage while undergoing paint removal that could degrade their structural integrity.

Many different methods have been used to remove painted coatings. One type, the "particle medium blast" (PMB) method involves impinging the surface to be stripped with particles such as BB's, plastic media, steel shot, wheat starch, and/or sand. However, PMB methods that are energetic enough by themselves to remove hardened coatings such as paint may damage delicate surfaces such as are found on aircraft and automobiles if they are not carefully managed. For example, if the impinging particles dwell too long at one location, the impinged surface may become pitted or stress hardened. This is especially important with regard to the surfaces of aircraft since pitting or stress hardening may change the loading on that portion of the aircraft. PMB may also damage putty joints often found on aircraft between surface plates.

It is also known in the art to apply chemical compounds to painted surfaces in order to chemically breakdown the layers of paint, thereby stripping the paint away from the surface to be exposed. However, such compounds may pose a risk to human health, are usually toxic, and often not biodegradable. Overall, these types of compounds are difficult and costly to dispose of because they present serious environmental problems.

Mechanical paint removal techniques are also known in the art. For example, U.S. Pat. No. 4,836,858, entitled "Ultrasonic Assisted Paint Removal Method" discloses a hand held tool which uses an ultrasonic reciprocating edge placed in contact with the surface to be stripped. Unfortunately, employment of this tool is labor intensive and relies upon the skill of a human operator to use it effectively. Further, control of this tool is a problem when applied to aircraft because the aircraft surface may be damaged if there is excessive tool dwell at one location.

Radiant energy paint removal techniques are likewise known in the art. One such system uses a laser and video frame grabber in a video controlled paint removal system in which paint is stripped from a surface using the output of the laser to ablate the paint while a video camera converts images of the surface being stripped into electronic data signals. The data signals are used to control the laser output. A processor compares the data signals with parameters stored in a memory to determine whether sufficient paint has been removed from the surface being stripped If an insufficient amount of paint has been removed, then the surface continues being irradiated by the laser. If the irradiated area has been adequately stripped, the processor directs the laser to ablate another area. While the basic approach of ablating and "looking" to see if the proper amount of paint has been removed is sound, doing the looking using a video camera is extremely data intensive, requiring an enormous amount of data to be generated, gathered and analyzed in real time. Thus, real time control of video controlled paint removal systems is extremely difficult. What is needed, therefore, is a system and method wherein an ablation removal process can be easily controlled in real time without extensive data handling and processing requirements.

The difficulty associated with removing paint or other coatings is compounded when the basic substrate material over which the coating has been placed is non-metallic. For example, the use of composite structures is becoming increasingly more common. Such structures are typically manufactured, for example, of fiber reinforced epoxy or other thermoset or thermoplastic composites. Many aircraft and automobiles extensively employ plastic composites for surface structures. Such structures are painted for a variety of reasons including aesthetics, identification, and camouflage. However, such painted surfaces deteriorate under the action of weather and the mechanical forces to which they are subjected, thus requiring removal and replacement. Disadvantageously, other than hand sanding, there are no suitable methods for removing paint from the surfaces of such composites. PMB and mechanical grinding methods that are sufficiently energetic by themselves to remove the paint are also sufficiently energetic to damage the composite materials. Similarly, the use of chemical compounds to remove the paint is not a satisfactory solution because such chemicals tend to attack the composites, as well as the paint. Hence, there is a critical need in the art for a means for safely and efficiently removing paint or other coating materials from composite substrate materials without compromising the integrity of the underlying substrate composite material.

For a variety of reasons, then, known paint removal techniques for removing paint or other coatings from large surfaces, have not proven wholly satisfactory. It can thus be appreciated that coating removal, and particularly, the removal of paint from large and often delicate surfaces such as are found on aircraft and automobiles, is a problem that has not yet been satisfactorily solved.

SUMMARY OF THE INVENTION

The present invention advantageously provides a system and method for removing paint, or similar coatings, that address the above and other needs.

In accordance with one aspect of the present invention, pulsed light sources are used to remove coatings from substrates via the ablation method. For purposes of the present application, ablation is defined as the rapid decomposition and vaporization of a material resulting from the absorption of energy by the material and is associated with the generation of pressure waves radiating from the surface of the material The amount of material removed by the ablative process of the invention is controlled using a photodetector system that measures the color intensity of the light reflected from the substrate at the particular location where the material is being removed Advantageously, because most paint and other coatings can be differentiated by the color between, e.g., a topcoat(s) and a primer undercoat, or between an uppercoat and the substrate on which the coating is placed, the photodetector system is able to readily ascertain in real time when the topcoat(s) has been removed and only the primer undercoat remains, or when all the upper coats have been removed and only the substrate surface remains. Immediately upon making such a determination, i.e., immediately upon determining that only a primer undercoat remains, or that the substrate surface has just been exposed, appropriate control signals are generated which result in irradiation of another area of the substrate by the pulsed light source In accordance with another aspect of the invention, a pulsed light source in combination with a photodetector system is scanned across a work surface in a controlled manner so as to systematically remove all coatings on the work surface down to a prescribed color. Such prescribed color may advantageously be that of a prescribed undercoat, e.g., the primer coat, or that of the substrate. In some applications, the feedback provided by the photodetector system may also be used to indicate the character of the stripped work surface for quality control purposes. In addition, the photodetector system may sense position information on the work surface, which position information may be used by a robotic controller to control the scanning operation.

The coating removal system of the invention includes an ablation removal device, such as a flashlamp or a laser, and a photodetecting circuit, housed within a single scanning head. A flashlamp, or flashtube, is a gas filled device which converts electrical energy to optical energy by passing current through a plasma typically contained in a transparent tube through which the optical energy is transmitted. Appropriate control circuits and positioning devices, coupled to the scanning head, position the scanning head at a desired location above a work surface having coatings thereon that are to be removed, and generate the requisite control signals needed to operate the ablation removal device and the photodetecting circuit. Advantageously, the output signal(s) from the photodetecting circuit is (are) used as a feedback signal(s) to provide optical feedback to the circuits that control and position the ablation removal device, thereby enabling the scanning head to be effectively scanned across the work surface at a rate and with an incident intensity of the surface that efficiently and safely removes a desired coating from the work surface without damaging the work surface.

The photodetecting circuit of the invention includes at least one array of photodiodes. The photodiodes of each array are optically filtered so as to detect a prescribed wavelength, or band of wavelengths, representing a desired color, e.g., one of the primary colors, or other selected color. The photodiodes of each array are positioned so as to monitor reflected light energy from the work surface. Typically, the photodiode arrays are gated ON only at a time that allows them to sense or collect light energy associated with a trailing edge portion of the main optical pulse generated by the ablative device. Alternatively, a secondary or auxiliary light source within the scanning head may be pulsed ON at an appropriate time within the ablative removal cycle to adequately illuminate the work surface with sufficient viewing light to provide a source of reflected light suitable for detection by the photodiodes in the array.

The electrical signals generated by the photodiodes in response to sensing the reflected light of each array are converted to digital sensor data and processed by digital circuitry in a sensor controller. Parallel monitoring of the optical output from the ablative removal device provides a basis for normalizing the optical information from the photodiode arrays. The normalized sensor data is then temporarily stored and compared with permanently stored reference data representative of the desired color of the work surface once the prescribed coating has been removed therefrom. The results of this comparison form a basis for a feedback signal directed to a remote computerized controller. That is, since different coating layers as well as substrates are characterized by different colors and reflected optical intensities, the feedback signal affords a method for real time control of the coating removal process and allows selective removal of successive coating layers. Hence, the feedback signal may be acted upon by the remote computerized controller in order to control the ablation removal process in a desired manner. Further, as a function of the particular pattern of the photodiodes used in the photodetector arrays, the output signals from the one or more of the photodetector arrays allow optical information from the entire width of the irradiated surface on the structure to be processed. The area irradiated by the light source when the scan speed is zero is referred to as the "footprint." Optical information reflected from the "footprint" advantageously provides increased spatial resolution and sensitivity of the system to coating anomalies, e.g., repair patches on an aircraft skin that may have been hidden by subsequent over coats of paint. Moreover, such spatial capability provides a means for assisting a robotic controller, or equivalent positioning device controlled by the remote computerized controller, in maintaining the scanning head in a prescribed orientation, e.g., a level position, above the work surface.

In accordance with yet another aspect of the invention, appropriate cooling means for limiting the temperature of the structure in the vicinity of the irradiated area is also included within the scanning head. Such cooling means typically includes a nozzle for directing a particle stream, e.g., a jet of $CO_2$ pellets, at the area from which material has been ablated, as well as an appropriate vacuum system for removing all expended particles, gases, and vapors associated with the ablative removal process. The particle stream also advantageously cleans the ablated surface.

The present invention may be characterized, in accordance with one embodiment thereof, as a method for removing material from a structure. Such method includes the steps of (1) irradiating a target area of a structure having at least one layer of material formed on a substrate with radiant energy having an intensity sufficient to ablate the layer of material; (2) monitoring reflected radiant energy from the target area to sense the presence of a prescribed color intensity different from the color intensity of the layer of material being ablated; and (3) controlling the irradiation of the target area with the radiant energy in step (1) as a function of the color intensity sensed in step (2).

In accordance with another embodiment, the present invention may be characterized as a system for removing a layer of material from a structure. Such system includes: (a) irradiating means for irradiating a target area of a structure having at least one layer of material formed on a substrate with radiant energy having an intensity sufficient to ablate the layer of material; (b) monitoring means for monitoring reflected radiant energy from the target area for the presence of a prescribed color intensity different from the color intensity of the layer of material being ablated by the irradiating means; and (c) feedback means for controlling the irradiation of the target area with the radiant energy from the irradiating means as a function of the color intensity sensed by the monitoring means. The prescribed color, in turn, is detected through the use of photodetection means. Such photodetection means detects reflected radiant energy having a prescribed wavelength, where the prescribed wavelength is characteristic of the prescribed color. In a preferred embodiment, such photodetection means includes: (a) means for dividing the reflected radiant energy into a plurality of optical channels; (b) first detection means for detecting if the reflected radiant energy in each of the plurality of channels contains a respective wavelength; and (c) processor means for analyzing the respective wavelengths detected in each optical channel to ascertain whether the prescribed color intensity is present in the reflected radiant energy.

Still a further embodiment of the invention may be characterized as photodetector apparatus useful for examining the surface of a structure. Such photodetector apparatus includes: (a) illuminating means for illuminating a target area of the surface of the structure with pulsed radiant energy; and (b) monitoring means for monitoring reflected radiant energy from the target area for the presence of a prescribed color intensity.

It is thus a feature of the invention to provide a coating removal system and method wherein coatings may be selectively removed using a photodetector feedback system in conjunction with an ablation removal process.

It is another feature of the invention to provide such a coating removal system and method wherein a photodetector system ascertains the color intensity of the work surface from which the coatings are being removed, and uses such color intensity determination as an indicator of whether the coating has been sufficiently removed.

It is an additional feature of the invention to provide such a coating removal system and method that reduces the risk of damage to frangible substrates such as composites.

It is a further feature of the invention to provide such a coating removal system and method that includes in a single scanning head: (1) radiant energy ablative removal means, such as a flashlamp, for removing material coatings off of a work surface of a structure; (2) photodetector means for optically detecting when a desired coating has been stripped from the work surface; and (3) cooling and cleaning means for limiting the temperature of the structure and for removing any residue of the ablated material from the stripped work surface. Advantageously, such scanning head may be scanned across the work surface as a function of feedback signals sensed by the photodetector means.

It is another feature of the invention to provide a photodetector system that generates an output signal(s) that indicates the presence or status of substrate surfaces or coating layers of a structure. Such photodetector output signal(s) provide an indication of the color intensity of the work surface, which indication may advantageously be used for varied purposes. When the photodetector system is used as part of a coating removal system, for example, such output signal(s) may be used as a feedback signal(s) for one or more of the following purposes: (1) to control the coating removal process, i.e., to limit the exposure of the stripped surfaces or layers, thereby preventing damage to the work surface or coating layers; (2) to position and orient, e.g., level, the ablative removal system above a desired location on the work surface relative to topological landmarks on the work surface; (3) to enable the safe and efficient operation of the ablative removal device, as by, e.g., turning on the ablative removal device only when certain conditions are satisfied, and/or by controlling the output power of the radiated energy generated by the ablative removal device; (4) to provide real time feedback to a remote controller that controls the scan rate of the ablative removal device; or (5) to monitor the formation of frost and/or condensation on the work surface from the application of a particle stream, which particle stream may be used to cool and clean the structure. When the photodetector system is not used directly as part a coating removal system, or in addition to being used as part of a coating removal system, the output signal(s) from the photodetector system may also be used, for example, to monitor a previously stripped section of the work surface for the purpose of quality control or surface anomaly detection.

BRIEF DESCRIPTION OF THE DRAWINGS

The above and other aspects, features, and advantages of the invention will be more apparent from the following more particular description thereof, presented in conjunction with the following drawings, wherein:

FIG. 4 is a waveform timing diagram that illustrates one timing arrangement that may be used for operating the photodetector circuit in accordance with the present invention;

FIG. 5 is a waveform timing diagram that illustrates an alternative timing arrangement for operating the photodetector circuit;

FIG. 6 is a diagrammatic representation of one embodiment of the photodetector arrays;

FIG. 7 shows a diagrammatic representation of an alternative embodiment of a photodetector array of the present invention; and FIG. 8 is a flow chart that depicts the basic method used by the system shown of FIG. 1 to remove coatings from a substrate.

Like reference numerals are used to represent like elements in the various figures and the accompanying description that follows.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

It is noted that the present invention combines an ablative removal technique with a particular optical detection technique in order to remove one or more coatings from a substrate surface. Ablative removal techniques using radiant energy, e.g., a flashlamp, combined with a different type of detection system, are described in applicants' copending application entitled "Method and System for Control of a Material Removal Process Using Spectral Emission Discrimination", Ser. No. 07/813,865, filed concurrently herewith.

Figure 1:
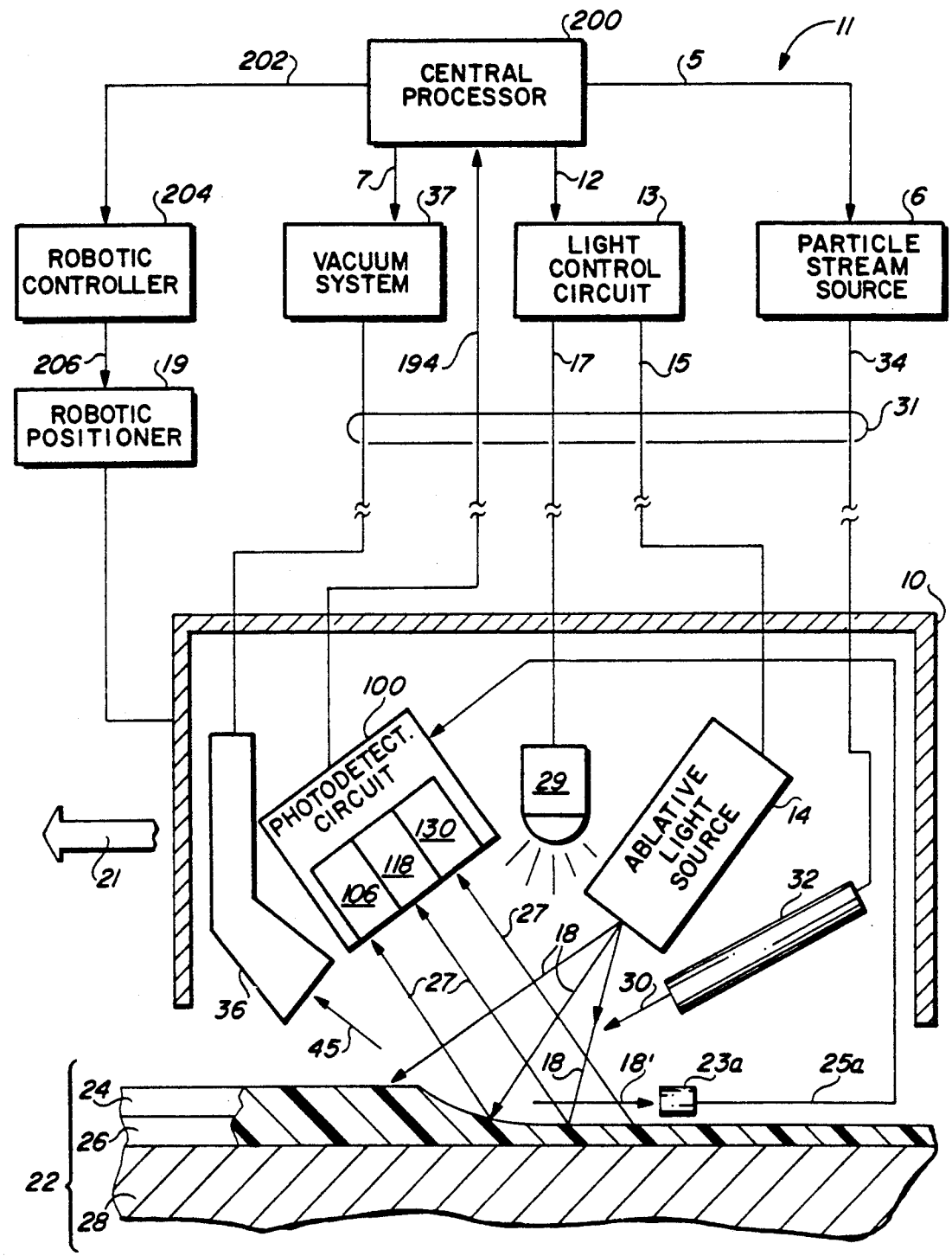
FIG. 1 is a block diagram that diagrammatically illustrates the main components of a coating removal system made in accordance with the present invention.

Referring first to FIG. 1, there is shown a block diagram that diagrammatically illustrates the main components of a coating removal system 11 made in accordance with the present invention. Advantageously, the system 11 removes coatings 24 and/or 26 from a substrate 28 without damaging the substrate. (Note, the coated substrate 28 may hereafter be referred to as the "work surface" or "structure" 22.) Further, the system 11 includes a digital control processor 200 that coordinates and controls the scan rate of optical energy 18 and particle stream 30 across the surface of substrate 22. Control is effected using feedback provided by an optical detecting circuit 100 that detects the optical character of the surface of the work surface 22.

Referring to FIG. 1, data processor 200 (which may be an IBM AT or AT compatible personal computer, or equivalent) generates output signal 5 to enable particle stream source 6, output signal 7 to enable vacuum system 37, output control signal 12 to control light control circuit 13 (which may be of a type well known by those skilled in the art), and output signal 202 to provide path and speed instructions to robotic controller 204. Particle stream source 6, in turn, is coupled to nozzle 32, which nozzle is adapted to direct a stream 30 of particles, explained more fully below, across the surface of the workpiece 22. Similarly, vacuum system 37 is coupled to exhaust nozzle 36, which exhaust nozzle is positioned to receive the residue 45 of any materials that are ablated by radiant energy 18 generated by ablative light source 14 and/or the spent particle stream. Light control circuit 13 generates a control signal 15 which establishes the repetition rate and pulse width of the output of ablative light source 14. In some embodiments of the invention, light control circuit 13 also generates another control signal 17 which turns on auxiliary light 29 for a desired time period during the coating removal cycle, as explained more fully below in connection with FIG. 5.

Nozzle 32, ablative light source 14, auxiliary light source 29 (when used), and exhaust nozzle 36 are all housed within a scanning head assembly 10 that is adapted to move above the work surface 22 as controlled by robotic positioner 19, as indicated by the arrow 21. Advantageously, electrical, optical, and other coupling to the elements within the scanning head assembly 10 is achieved through appropriate flexible cabling 31, thereby facilitating movement of the scanning head assembly, including the elements housed therein, while allowing the control circuits for such elements, such as the particle stream source 6, the light control circuit 13, and the vacuum system 37, to be stationary at a position remote from the scanning head assembly 10.

In order to provide a feedback signal to the system 11 that allows it to control the coating removal process, a photodetecting circuit 100 detects the optical condition at the work surface 22 by monitoring radiant energy 27 reflected from the work surface 22. The photodetecting circuit 100 receives the optical signals and generates electrical feedback signal(s) 194 therefrom that are conveyed to the control processor 200. The control processor 200 processes the feedback signals 194 and converts them into a composite output signal 202. Robotic controller 204 transforms signal 202 into control or instructional signals 206 that direct the path and speed of robotic positioner 19. Such instruction signal 206 directs robotic positioner 19 to move the scanning head assembly across the work surface 22 so as to effectively scan ablative energy source 14 and particle stream 30 across the surface of the structure 22 in accordance with a prescribed pattern. The path of robotic controller 204 is determined in accordance with a suitable path generating processing routine implemented by data processor 200 in accordance with techniques well known by those skilled in the art. photodetector circuit 100 is preferably located within or attached to the scanning assembly 10, with the output signal 194 of the photodetector circuit 100 being coupled to the remotely positioned control processor 200 through appropriate flexible electrical cable.

Figure 2:
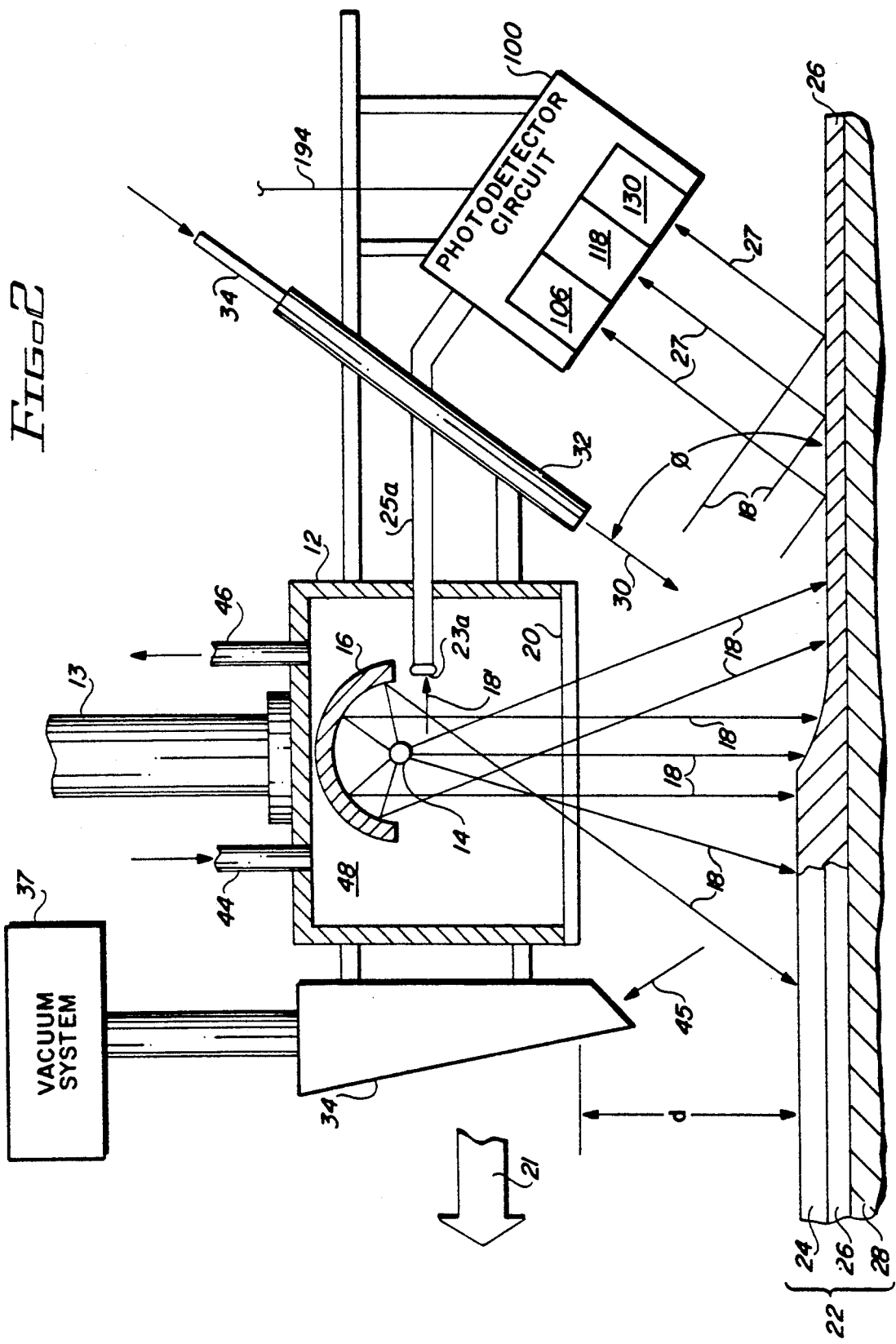
FIG. 2 is a schematic diagram of the scanning head used with the coating removal system shown in FIG. 1.

Referring next to FIG. 2, there is shown a schematic diagram of the scanning head assembly 10 used with the coating removal system 11. As seen in FIG. 9, the scanning head assembly 10, comprising optical energy source 14 and reflector 16, is supported by robotic positioner 13 at a predetermined standoff distance "d" from the surface of structure 22. The optimum standoff distance "d" for ablative removal of coatings is a function of the amount of output power contained in the radiant energy 18 output by the ablative energy source 14. In general, the closer the source 14 is positioned to the work surface 22, the more power there is to ablate the upper coatings 24 and/or 26 covering the substrate 28. However, care must be exercised to prevent too much ablative power from being delivered, else more than the desired coating(s) may be ablated. While the ablative power may be controlled by adjusting the repetition frequency and pulse width of the light 18 generated by the light source 14, the intensity of optical energy 18 incident on the surface of structure 22 is preferably controlled by simply controlling the standoff distance "d". Initially, an approximate distance "d" for nominal output power levels of the light source 14 is determined experimentally. For example, where the ablative energy source is a flashlamp, as described in applicants' copending applications referenced above, and where such flashlamp provides an incident intensity at the surface of the structure of about 1–10 joules/cm$^2$ and has a pulse width that may range from about 1000–2400 microseconds ($\mu$sec) and a repetition rate of 4–5 Hz, and further where a coating of paint having a nominal thickness of 4–8 mils overlays an aluminum substrate, the initial standoff distance "d" is on the order of 1 to 3 cm.

Robotic positioner 19 is controlled to move the assembly 10 along a predetermined path at a controlled scan speed over the surface of structure 22 so that ablative energy source 14 and particle stream 30 may be directed to scan and impinge, respectively, the coating or coatings formed on the surface of substrate 28. The radiant energy (light) 18 from the source 14 ablates the coating to be removed in the immediate area of exposure to the radiant energy 18. The particle stream 30 limits the temperature rise of structure 22 as a result of absorbing optical energy in the form of heat provided by light 18. Robotic positioner 19 may be implemented as a CIMROC 4000 Robot Controller manufactured by CIMCORP Precision Systems, Inc., Shoreview, Minn. The scan speed is functionally related to the output signal 194 by a function bounded by upper and lower limits, as described more fully in the referenced patent application. Such function may be increasing or decreasing, depending on the particular application. Material removed from the surface of substrate 28 and the expended particle stream 30 after it impinges structure 22 are collected by vacuum system 37 through nozzle 25 mounted to housing 12.

Particle stream 30 is provided by particle stream source 6 which may provide gas, liquid, or solid particles, or any combination of particles. For example, particle stream source 6 may be a gas tank if particle stream 30 is a gas, or a carbon dioxide pellet source of the type commercially available from Cold Jet, Inc., of Loveland, Ohio. The particles which comprise particle stream 30 are delivered to nozzle 32 via duct 34.

Note that as depicted in FIGS. 1 and 2, the system 11 is configured to remove an upper layer 24 from the substrate 28 while leaving a lower layer 26, e.g., a primer paint coat. Such removal is only exemplary, as the system 11 could just as easily be configured to remove both layers 24 and 26, leaving the surface of the substrate 28 exposed. The mechanism by which the system 11 determines when the proper layer has been ablatively removed is to monitor light 27 reflected from the surface 22 for a specific color and intensity, i.e., color intensity. Such monitoring assumes, of course, that a distinguishing color intensity difference exists between the layer 26 to be removed and the layer 24 to remain, or between the layers 24 and 26 to be removed and the substrate surface. This assumption will almost always be true. The reflected light 27 is detected, collected, and analyzed by photodetector circuit 100. The reflected light that is monitored may be either the trailing edge of the ablative light pulse 18, as explained more fully below in connection with FIG. 4, or light obtained from an auxiliary light source 29, as explained more fully below in connection with FIG. 5.

Regardless of the source of the reflected light 27, the reflected light is monitored by the photodetector circuit 100 for the presence of a specific wavelength, or a band of wavelengths, characteristic of the color of the layer or surface that is to remain. Immediately upon detection of such characteristic wavelengths, the control processor 200 is notified via the signal 194 so that it knows that sufficient material has been removed at the present location of the incident radiant energy 18. Thus, the control processor 200 immediately generates the requisite control signals so as to move the scanning head 10 to a new location, adjust the scanning speed, and/or adjust the output power of the light source 14, in order to assure that no further material is removed at the location where the characteristic wavelength was detected.

In the preferred embodiment, as seen in FIG. 2, photodetector circuit 100 is attached to the outside of a water cooled housing 12 wherein the light source 14 is housed. Water, or other suitable coolant, enters and exits the housing 12 through parts 44 and 46. Photodetector circuit 100 is mounted to the exterior of housing 12 such that it is able to detect reflected light 27 from the surface of structure 22. Advantageously, the particle stream 30, directed at the surface 22 at an approximate angle $\theta$, helps to keep the lens cover 20 of the housing 12 clean from debris and other foreign matter that might otherwise accumulate thereon. The angle $\theta$ will typically range from 5 to 60 degrees, but is not felt to be critical for ablation as described herein.

Photodetector circuit 100 should be oriented to receive reflected light from immediately behind the same area impinged by the incident ablative light source 18. In some embodiments, in order to monitor the status or condition of the surface 22 over a wide "footprint", it is desirable that the reflected footprint area, i.e., that area from which the reflected light 27 is received, actually be somewhat larger and behind the irradiated footprint. The irradiated footprint may be referred to as the "target area" because it is the area at which incident light 18 is directed. For such wide area monitoring to provide useful information, it is necessary that the photodetector circuit 100 have spatial distribution resolution capabilities so that it can detect not only the presence of a characteristic wavelength, but also a particular narrow area or region within the monitored area whereat the characteristic wavelength originated. Such spatial distribution resolution is advantageously provided by using a plurality of photodetectors arranged in a suitable pattern within a photodetector array, as described more fully below in conjunction with FIGS. 6 and 7.

Further details associated with the scanning head assembly 10, and its manner of use, may be found in applicants' aforementioned patent applications. In particular, a preferred ablative light source 14 is a water-cooled flashlamp that is housed within a custom housing as described in the cited patent applications. A suitable flashlamp for use within such a housing is available from Maxwell Laboratories, Inc., of San Diego, Calif., and is described in commonly assigned U.S. patent application Ser. No. 07/645,372, filed Jan. 24, 1991 U.S. Pat. No. 5,126,621, which patent application is also incorporated herein by reference.

The photodetector circuit 100 will next be described. It is the function of the photodetecting circuit 100 to detect the optical character of the surface of structure 22. In its simplest form, the photodetector circuit 100 simply includes a single photodiode selected to detect a particular characteristic wavelength. Wavelength selection is made by choosing a particular photodiode/lens/filter combination (which are commercially available components), or by selecting a broadband photodiode and manually placing a removable or replaceable filter in the optical path leading to the photodiode. In this manner, only optical signals of the characteristic wavelength successfully pass through the filters and are detected by the photodiode. All other optical signals are blocked by the filter. Thus, if it is known that the primer coat is blue, for example, and if it is desired that the primer coat remain, then a blue filter may be placed in front of the photodiode so that the photodiode only detects blue light. If a subsequent coating removal operation requires that all layers be removed down to the substrate, and if the substrate is, e.g., yellow, then the blue filter may be removed and replaced with a yellow filter., i.e., a filter, or combination of filters, that only allows yellow light to pass therethrough.

Figure 3:
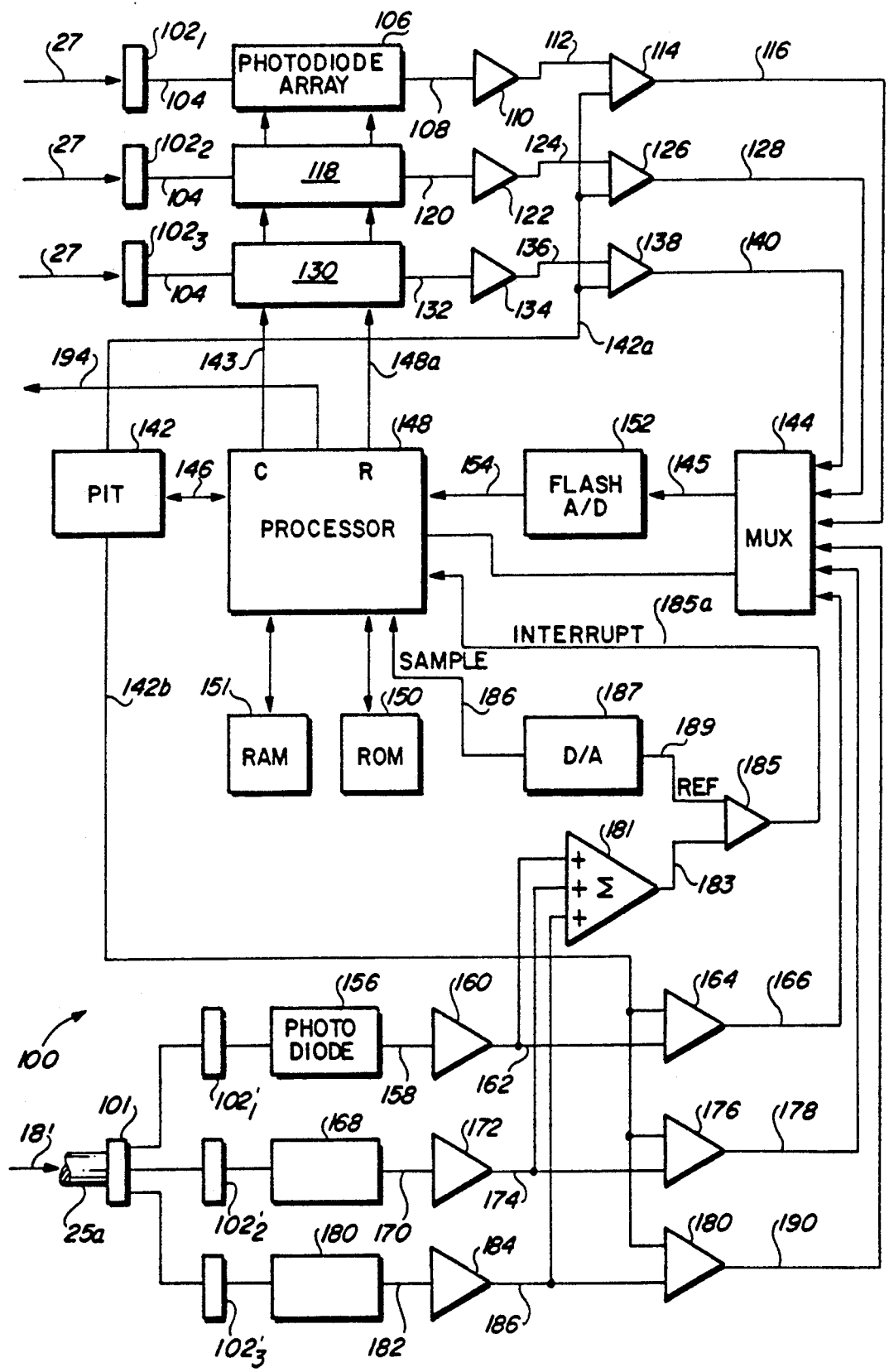
FIG. 3 is a block diagram of the photodetector circuit.

Using a single photodiode as the photodetecting circuit 100 only provides limited resolution of the reflected light to be analyzed, and does not provide additional information, such as spatial distribution data, that may be detected. Hence, it is preferred that more than one photodiode be used, and that an appropriately processed optical, digital output signal 194 be generated from all of such photodiodes. For example, a digital weighted sum average ("WSAV") signal may be generated from all of the output signals from the individual photodiodes in the array. A block diagram of one type of photodetector circuit 100 that achieves this function is shown in FIG. 3. As seen in FIG. 3, the reflected light 27 from the surface 22 is received by filters 102. As seen in FIG. 3, at the heart of photodetecting circuit 100 is a processor 148. Such processor 148 may be realized using any suitable microprocessor circuit capable of operating at a modest clock speed, e.g., 5-10 MHz. By way of example, processor 148 may be implemented using an Intel 8X51FB imbedded processor. Coupled to the microprocessor 148 is a conventional random access memory (RAM) 151, a conventional read only memory (ROM) 150, an analog-to-digital (A/D) converter 152, and an analog multiplex circuit (MUX) 144. The incoming light signals are split into three optical data channels. Each channel is designed to select a particular characteristic wavelength, or band of characteristic wavelengths. For example, the channels may be respectively designed to receive and process wavelengths characteristic of the color intensities associated with red, blue or yellow. In this manner, photodetecting system 100 is able to receive and analyze optical energy intensities from selected portions, or from all, of the entire optical portion of the electromagnetic spectrum.

The optical data received in each data channel is filtered and continuously monitored by photodiodes contained in the photodiode arrays 106, 118 or 130, and is temporarily stored in response to receiving an appropriate clock or shift signal obtained from the processor 148. Each photodiode in the array, as explained more fully below, represents the filtered light intensity received from a defined area or "pixel" of the reflection footprint, i.e., the monitored area from which the reflected light 27 is received. The data temporarily held in the photodiode arrays is then serially transferred, under control of the processor 148, through appropriate channels, including the MUX 144 and the A/D 152, into the processor 148. The processor 148 processes the data in a prescribed manner. For example, the processor may divide the signals received in each data channel by a corresponding normalization signal obtained from a sample optical energy 18' of the light 18. Sample optical signal 18' is provided to photodetecting circuit 100 through lens 23a and fiber optic bundle 25a. Fiber optic bundle 25a may penetrate housing 12 as shown in FIG. 2. Optical energy 18' is filtered and provided to photodiode circuits 156, 158 and 180, and is used to normalize the amplitude of received signals so that each is independent of variations in the incident light intensity.

As seen in FIG. 3, each optical data channel includes an optical filter $102_i$ that attenuates all light except light of the characteristic wavelength that is received from the reflection footprint. Preferably, at least a portion of the reflection footprint is located somewhat behind the area on structure 22 which is impinged by particle stream 30. Filters $102_i$ are available commercially from numerous vendors for any desired wavelengths. The light that passes through the filter $102_i$ is received and temporarily held in a photodiode array 106, 118, or 130. By way of example, the photodiode array may be a 1×n photodiode array, where n is a positive integer, as for example 1024. The photodiode array receives and transforms any received light 104 transmitted through filter $102_i$ into a series of electrical pulses 108 having amplitudes corresponding to the intensity of the received light, as controlled by an appropriate clock signal 143 generated by the processor 148. The rate of the clock signal 143, by way of example, may range from 2-25 MHz. The electrical pulses 108 are amplified in amplifiers 110, 122 or 134. Track-and-hold circuits 114, 126 or 138, receive signals 112, 124 or 136 and generate a DC analog signal 116, 128 or 140 that corresponds to the average peak pulse amplitude of electrical pulse train 112, 124 or 136 in response to receiving a hold signal 142a from parallel interrupt timer (PIT) 142.

Analog signals 116, 128, and 140 are coupled through MUX 144 to flash A/D converter 152 over signal line 145. Control of MUX 144 is effected by signals 147 generated by processor 148. The A/D converter 152 thus generates a digital data stream 154 corresponding to the signals 116, 128, or 140 that is directed as an input signal to processor 148. Processor 148, operably coupled to RAM 151, stores the digitized optical data thus received in RAM 151. ROM 150 has stored therein a suitable operating program that controls the operation of the processor 148.

Photodetecting circuit 100 also includes a plurality of ablative light source reference channels. Each such sample channel includes a photodiode circuit, 156, 168 and 180, with each receiving as an input a sample 18' of optical energy 18 directed to the surface 22 through lens 23a (FIG. 2) attached to optical fiber 25a and splitter 101 (FIG. 3). Each sample channel further includes an appropriate optical filter $102_1'$, $102_2'$, or $102_3'$ that filters out all but a desired wavelength or band of wavelengths. The photodiode circuits 156, 168 and 180 function similar to the photodiode arrays 106, 118, and 130, transforming any light transmitted through the filter $102_1'$, $102_2'$, or $102_3'$, into a series of electrical pulses having amplitudes corresponding to the intensity of the transmitted light. Electrical pulses 158 are provided to amplifiers 160, 172 or 184. The resulting amplified pulse train is directed to track-and-hold circuits 164, 176 or 180 which generate DC analog output signals 166, 178, and 190 representing the peak pulse amplitude of the amplified pulse trains in response to receiving hold signal 142b from PIT 142. The signal thus generated for each sample channel is provided to MUX 144.

The photodiodes 156, 168, and 180, and their associated filters $102_1'$, $102_2'$, and $102_3'$, respectively, receive sample optical signal 18'. In this way, the signals directed to the MUX 144 through the respective sampled light data channels correspond to a sample of the light source used to provide the reflective light 27 to the photodetector circuit 14. Such sample of optical signal 18' is used to normalize the light detected through photodiode arrays 106, 118, and 130 so that variations in the intensity of the incident light source do not adversely affect the processing of signals 116, 128, and 140 into an appropriate output control signal 194.

As also seen in FIG. 3, a summing amplifier 181 sums the output of the respective sample channel amplifiers 160, 172 and 184. The resulting summed output signal is directed over signal line 183 to one input of a threshold detector 185. The other input of the threshold detector 185 is a reference voltage that is generated by digital-to-analog (D/A) converter circuit 187 as a function of a digital reference signal 189 determined by the processor 148 and conveyed to D/A circuit 187 via signal line 186. The signal 189 is provided only during a sample window. Hence, the threshold circuit 185 receives the reference voltage that enables it to respond to the summed output signal 183 only during such sample window. If the summed output signal 183 exceeds the threshold reference voltage during the sample window, which only happens if there is incident light present during the sample window, then the output of the threshold detector 185 goes high and functions as an interrupt signal to the processor 148 causing it to enter a data sample mode.

In the data sample mode, the processor 148 serially receives optical data from the photodiode arrays 106, 118 and 132 through the optical input channels and stores such data upon receipt of a reset signal 198a generated by processor 148. Also during the data sample mode, sample optical data may be received from the photodiodes 156, 168 and 180 through the sample channels. Parallel interrupt timer (PIT) 142 controls the timing of the particular data streams which are read by processor 148 and stored in RAM 151 by hold signals 142a so that, for example, data originating from a first input channel including photodiode array 106 and photodiode 156, are read together. PIT 142 similarly controls when processor 148 reads data from the second input channel that includes photodiode array 118 and photodiode 180, and from the third input channel, which includes photodiode array 118 and photodiode 168.

The processing routine stored in ROM 150 and implemented in processor 148 causes processor 148 to determine the quotients of: signal 140 divided by signal 190, signal 128 divided by signal 178, and signal 116 divided by signal 166, in order to normalize the outputs of the photodiode arrays for variations in the intensity of the output of light 14. Signals 166, 178, and 190 need be sampled only once every data sample cycle, e.g., once every 100 clock signals 143 if photodiode arrays 106, 118, and 130 each have, for example, 100 diodes. Such normalization allows photodetecting circuit 100 to evaluate the optical character of the surface of structure 22 as the output of light source 14 degrades over time.

The processor 148 generates the output signal 194 and transmits such signal to the control processor 200. If needed, such signal can be converted to an optical signal using an appropriate conversion circuit in order to allow the transmission of the signal to be done optically over a fiber optic transmission cable, thereby rendering the signal much more immune to electromagnetic noise. If so converted, an appropriate optical receiver circuit is used at the other end of the transmission line in order to convert the signal back to an electrical signal suitable for use by the control processor 200. Fiber optic transmitters and receivers suitable for such purpose may be implemented using, e.g., a Litton Fiber Optics Transceiver, Model E03675-2.

By way of example, signal 194 may represent a weighted sum average, "WSAV$_{color}$", as determined by processor 148 in accordance with the equations below for each color channel, where "color" corresponds to the narrowband portion of reflected light 27 detected by a particular photodiode array:

$$WSAV_R = \frac{\sum_{i=1}^{m} \left( \frac{\text{Signal}116i}{\text{Signal}166} \right)}{m} \quad (1)$$

$$WSAV_Y = \frac{\sum_{i=1}^{m} \left( \frac{\text{Signal}128i}{\text{Signal}178} \right)}{m} \quad (2)$$

$$WSAV_B = \frac{\sum_{i=1}^{m} \left( \frac{\text{Signal}140i}{\text{Signal}190} \right)}{m} \quad (3)$$

where i represents a particular photodiode in the photodiode arrays, m represents the number of photodiodes in photodiode arrays 106, 118, and 130, and "R", "Y", and "B" represent the red, yellow, and blue components, respectively, of signal 27 as detected by photodiode arrays 106, 118, and 130, respectively. Thus, the weighted sum average for each channel corresponds to the average intensity of a given set of light data detected by a particular photodiode array.

The value of the weighted sum average ("WSAV") from the optical channel detecting the information of interest may be used to determine an appropriate scan speed for optical energy source 14, or provide other suitable control functions. For example, if photodiode array 106 detects optical energy from the red portion of the visible portion of the electro-magnetic spectrum, and the reflected optical characteristic desired to be detected from the surface of a structure, such as structure 22, are colored red, then the weighted sum average for the red channel may be used to determine the scan speed of the optical energy source 14, as described in greater detail further herein.

The processor 200 (FIG. 1) uses information contained in the signal 194 received from the photodetector circuit 100 as a feedback signal to generate an address for a look-up table stored in the processor 200. The look-up table contains scan speeds corresponding to the particular address used. Thus, when addressed, the contents of the addressed cell of the look-up table are retrieved and transformed into suitable scan speed control signals that comprise, in part, signal 202, directed to the robotic controller 204.

The control signal 202 comprises a composite control signal that also includes "path" control instructions. Thus, composite signal 202 provides both path and speed control instructions to robotic controller 204. Robotic controller 204 then generates command signals 206 that direct the operation of robotic positioner 19, which may be implemented using a CIMROC 4000 Robot Controller manufactured by CIMCORP Precision Systems, Inc., Shoreview, Minn. A suitable robotic controller is typically included as part of any robotic system sold by vendors of commercial robotic positioners.

Thus, in summary, the purpose of robotic positioner 13 is to position the scanning head 10 so that the surface of structure 22 is scanned with optical energy 18 provided by ablative energy source 14 and particle stream 30 in a predetermined path at a scan speed dependent on the optical character of the surface of the structure 22 as determined by photodetecting circuit 100. The scan speed is controlled so that substrate 28 of structure 22 is not damaged as a result of structure 22 absorbing excessive optical energy which is transformed into heat.

The temperature gradient through structure 22 is controlled to prevent damaging substrate 28 while layers 24 and/or 26 are being removed to expose layer 26 or substrate 28. Two approaches may be used to achieve this purpose. In a first approach, the speed at which the scanning head is moved across the surface 22 is controlled by determining an appropriate scan speed, stand-off distance "d", mass flow rate and temperature of particle stream 30. This approach is described in applicants' aforecited patent applications. In a second approach, the scanning head may be incrementally moved across the surface 22 in small discrete distances. Also, the duty cycle of the ablative light pulses may be controlled to prevent excessive temperatures in the substrate. This incremental approach is described further below in conjunction with FIG. 8.

Turning next to FIG. 4, there is shown a waveform timing diagram that illustrates one timing arrangement that may be used for operating the photodetector circuit in accordance with the present invention. As seen in FIG. 4, an ablation light pulse 220 is generated beginning at a time T1. Such light pulse is emitted from the ablative light source 14. During the trailing edge of the ablation light pulse 220, i.e., at a time T2 seconds after the start of the pulse 220, interrupt signal 185a is generated by comparator 185, as represented by sample pulse 222. If, for example, the light pulse 220 has an approximate duration of 1000 microseconds, then the time T2 may lie in the range of 800-900 microseconds. Such interrupt signal 185a defines the sample window referred to above that places the photodetector circuit 100 in its data sample mode. Further, because the sample window occurs while the ablative light pulse is still present, the light from the light pulse 220 may be used to provide the source of the reflective light 27 used to examine the color of the surface 22. The ablative removal cycle comprises the time, T4, between ablative pulses 220. Such time T4 may be selected to be any suitable value to provide the necessary power output, but typically will range from about 10 to 5000 microseconds, corresponding to an ablative pulse rate of between 0 to 1000 Hz, where a pulse rate of 0 Hz corresponds to a single pulse.

In applications where light source 14 is a gas filled flashlamp for generating pulsed light, the data sample mode may correspond to a period when the optical energy generated by the flashlamp is at or near a minimum, as for example, at a level corresponding to amplitude 220a, shown in FIG. 4. As is well known, the output of a flashlamp is at a minimum when the flashlamp is energized by a "simmer" current. The "simmer" current is that level of current sufficient to maintain the gas contained in the flashlamp tube in an ionized state. Even when energized with a simmer current, a typical flashlamp would still generate sufficient optical energy to illuminate the surface of the structure being processed. In some applications of the present invention, it may be desirable for the data sample mode to correspond to an interval in the pulse period of the flashlamp when the flashlamp is energized by the simmer current. Such interval would be established by selecting an appropriate sample window, as previously discussed.

Referring to FIG. 5, a waveform timing diagram is shown that illustrates an alternative timing arrangement for operating the photodetector circuit 100 when an auxiliary light source 29 is used. As seen in FIG. 5, ablative pulses 220 are generated at an appropriate rate defined by the ablative period T4. At sometime after the control pulse 226 has gone low, the auxiliary light 29 is pulsed ON by control pulse 17, provided by light control circuit 13 in response to receiving signal 12 from control processor 200. Control processor 200 generates such signal 12 based on the value of signal 194 provided by photodetecting circuit 100. While the auxiliary light is ON, a photodetector sample pulse 230 is generated, corresponding to interrupt signal 185a, which effectively places the photodetection circuit in the data sample mode. In such mode, the photodetection circuit examines the reflected light 27 to determine the character of the surface 22. Thus, as seen for the approach shown in FIG. 5, the ablative process comprises ablating the surface material and looking to see if sufficient material has been removed.

FIG. 6 shows a diagrammatic representation of one embodiment of the photodetector arrays 106, 118 and 130 that may be used with the photodetector circuit 100 of the present invention. As seen in FIG. 6, the reflective light 27 is received in parallel by filters, $102_1$, $102_2$, and $102_3$, also referred to in FIG. 6 as filters F1, F2 and F3. Each filter is selected to pass only a wavelength or band of wavelengths characteristic of a prescribed color to be detected at the surface 22 being ablated. The light passing through each filter is then focused to fall upon an m×n photodiode array 106, 18 or 130, where m and n are integers. Using an m×n photodiode array in this manner offers the advantage of being able to detect the relative spatial position of the reflected light from the surface 22 of the material being ablated, as well as its color characteristics. For example, if the reflection footprint is optically focused to cover the entire surface area of the detector 106, and if such reflection footprint is larger than the irradiated footprint, then an area 221 may appear on the surface of the detector 106 that represents the ablated area, as measured by the wavelength that passes through the filter F1, while the area around the perimeter of the area 221 on the surface of the detector 106 would represent the non-ablated area. In other words, some of the individual photodiode elements that make up the surface of the diode array 106 would receive light of the passed wavelength, and others would not. In this manner the array 106 is able to provide a rough pixel-by-pixel resolution of the surface 22 of the material being ablated as seen through the particular wavelength that the array 106 is adapted to receive. When such information is combined with the other arrays 118 and 130, a great deal of information can be learned about the character of the surface 22 being examined by the incident light 18.

As will be appreciated by those of skill in the art, when a photodiode array is used as described in FIG. 6, a somewhat different data processing scheme may be employed than is described above in connection with FIG. 3 in order to process and analyze the array data. However, such processing schemes are well known in the art, and are commonly used to process the data obtained from large diode arrays, such as CCD arrays, in imaging applications.

With an array as shown in FIG. 6, the present invention provides more than just an ablative coating removal system. This is because the photodetector circuit 100 may be used independent of a coating removal system to examine the character and quality of surfaces, e.g., for quality control or damage control purposes. When used as a photodetector system in this manner, all that is required is to pulse ON the auxiliary lamp 29, or other non-ablative light source, and direct such light to the surface to be examined so that it is reflected therefrom to the photodetector circuit 100. The photodetector circuit 100 then processes the received reflected light in the manner described above to determine the character (color) of the surface being examined. Further, when used as part of an ablative coating removal system, the additional spatial distribution information provided by the individual diodes of each array provides a much more complete "picture" of the effectiveness of the coating removal process, and further helps the control processor 200 to better define an appropriate scan path. Moreover, such additional spatial distribution data allows the control system 200 to level, or otherwise orient, the scanning head 10 relative to the scanned surface of the structure 22.

FIG. 7 shows a diagrammatic representation of an alternative and simplified embodiment of a photodetector array of the present invention. As seen in FIG. 7, a single m×n detector 106' is utilized to receive reflected light 27 from the surface of structure 22. An appropriate lens assembly 101' focuses the light 27 through a replaceable filter assembly 102, and onto the surface of the array 106'. The replaceable filter assembly 102' is selected to pass only those wavelengths characteristic of a particular known surface that is to remain after one or more over coats are removed using the ablation process of the present invention. The simplified embodiment of the detector array shown in FIG. 7 may be used, for example, when the ablative removal process is being used to remove paint down to the primer coat from a large number of airplanes or automobiles, all of which have the same color of primer coat. Should the need arise to ablate away coatings down to a different color undercoat or substrate surface than can be detected by filter assembly 102', then the filter assembly 102' is simply replaced with an alternative filter assembly that can detect such different color.

Referring next to FIG. 8, a flow chart is shown that depicts one method that may be used by the present invention to ablatively remove coatings from a substrate. As seen in FIG. 8, a first step of the method, shown at block 302, involves the setting of initial parameters used to get the process started. Such initial parameters include, for example, the coordinates of a starting location for positioning the scan head, the scan path, an initial standoff distance "d", an initial ablative pulse energy (amplitude and pulse width), and an initial ablative pulse duty cycle (frequency). The initial parameters also include setting an index control variable, "i", to a starting value, such as 0.

Once the initial parameters are set, the scanning head is moved to the starting location of the prescribed scan path, L: (block 304). Once moved to this position, the timing circuits within the processor 148 (FIG. 4) determine whether it is time to generate an ablation pulse (block 306). An ablation pulse may be generated, for example, at a frequency of 4-5 Hz. When it is time to generate the ablation pulse, such a pulse is generated (block 308) having a pulse width and amplitude as controlled by the parameters previously set. After the ablation pulse has been generated, the incident light used to illuminate the area being ablated is summed for each light channel that is used (block 310). As explained above, in one embodiment, such incident light may be derived from the trailing edge of the ablation pulse (FIG. 4). In another embodiment, such incident light may be derived from an auxiliary light that is pulsed on at an appropriate time (FIG. 5). In either event, if it is time to sample the reflected light, determined at block 312, then a determination is made as to whether the sum of the incident light intensity, performed at block 310, is greater than a prescribed threshold (block 314). If not, then that means that there will be no reflected light of sufficient amplitude to provide any useful information. Hence, the reflected light is not monitored, and control of the process returns to block 306, waiting for the generation of the next ablation pulse. If the sum of the incident light intensity is greater than the prescribed threshold (block 314), then the data collection mode of the photodetector circuit 100 is begun (block 316).

Once the data collection mode has been initiated, the reflected light intensity from each channel is received and stored (block 318) as digital data. As this is being done, a determination is made as to whether such data should be normalized (block 320). If so, a normalization process is carried out (blocks 322, 324). The data from each channel is then analyzed to determine if it is characteristic of a prescribed wavelength, $\lambda$, representative of a prescribed color (block 328). If not, then the ablation parameters are adjusted (block 330), as required, and the next ablation pulse is generated (blocks 306, 308). If so, then a determination is made as to whether the scan path has been completed (block 332). If not, the index is incremented (block 334), the scanning head is moved to the next scan path location, $L_i$ (block 304), and the process repeats. If the scan path has been completed, i.e., if all locations along the designated scan path have been ablated, then the process is stopped.

As thus described in FIG. 8, the scanning head is incrementally moved along a desired scan path, with the scanning head being positioned at specified locations along the scan path only for so long as is required to ablate the desired layer(s) at that location. The desired ablation may require a single ablation pulse, or multiple ablation pulses, with the determination as to whether the layer has been removed being made by analyzing the reflected light from the ablated location for the presence of a prescribed color.

Not included in FIG. 8 is the control for the particle stream 30. It is contemplated that the particle stream 30 may be enabled at all times during the ablative removal process. If so, and if the stream is made up of $CO_2$ pellets or cold gases, frost or condensation may form around the ablative site. Advantageously, the photodetector circuit 100, while performing its monitoring function, can ascertain if such frost or condensation has formed, and if so, an appropriate control signal can be generated to make appropriate adjustments, e.g., turn OFF the particle stream for an appropriate time.

As thus described, it is seen that the present invention provides a coating removal system and method wherein coatings may be selectively removed using a photodetector feedback system in conjunction with an ablation removal process.

It is further seen that such coating removal system and method ascertains the reflected optical character or color intensity of the work surface from which the coatings are being removed, and uses such color intensity determination as an indicator of whether the desired coating has been removed. Advantageously, such approach reduces the risk of damage to the substrate, particularly frangible substrates such as composites.

It is further seen from the above description that the present invention provides a coating removal system and method that includes in a single scanning head: (1) radiant energy ablative removal means, such as a flashlamp, for removing coatings off of a work surface; (2) photodetector means for optically detecting when a desired coating has been stripped from the work surface; and (3) cooling and cleaning means for limiting the temperature depth profile of the ablated material from the structure and for cleaning the surface of the structure. Advantageously, such scanning head may be scanned across the work surface, either continuously or in step-wise fashion, as a function of feedback signals sensed by the photodetector means.

It is also seen from the above description that the invention provides a photodetector system that generates an output signal indicative of the presence or status of substrate surfaces or coating layers. Advantageously, the photodetector output signal provides an indication of the reflected color intensity of the work surface, which color intensity indication in turn may be used for a wide variety of purposes. As described, for example, when the photodetector system is used as part of a coating removal system, the output signal may be used as a feedback signal. As a feedback signal it may be used to: (1) control the coating removal process, i.e., to limit the exposure of the stripped surfaces or layers, thereby preventing damage to the work surface or coating layers; (2) position and orient, e.g., level, the ablative removal system above a desired location on the work surface relative to topological landmarks on the work surface; (3) enable the safe and efficient operation of the ablative removal device, as by, e.g., turning on the ablative removal device only when certain conditions are satisfied, and/or by controlling the output power of the radiated energy generated by the ablative removal device; (4) provide real time feedback to a remote controller that controls the scan rate of the ablative removal device; or (5) monitor the formation of frost and/or condensation on the work surface from the application of a particle stream, which particle stream may be used to cool and/or clean the work surface.

Finally, it is seen from the above description that when the photodetector system is not used directly as part a coating removal system, or in addition to being used as part of a coating removal system, its output signal may still be used, for example, to monitor a previously stripped section of the work surface for the purpose of quality control or surface anomaly detection.

While the invention herein disclosed has been described by means of specific embodiments and applications thereof, numerous modifications and variations could be made thereto by those skilled in the art without departing from the scope of the invention set forth in the claims.

What is claimed is:

1. A method for the selective removal of a material from a structure, comprising the steps of:
   (1) irradiating a target area of a structure having at least one layer of material formed on a substrate with a pulse of incident radiant energy generated by a flashlamp, said pulse of radiant energy having an intensity sufficient to ablate said layer of material;
   (2) monitoring radiant energy from said flashlamp that is reflected from said target area in order to sense the presence of a prescribed color intensity different from a known color intensity of the layer of material being ablated; and
   (3) controlling the irradiation of the target area with said radiant energy in step (1) as a function of the color intensity sensed in step (2).

2. The method as set forth in claim 1 wherein the step of monitoring the radiant energy reflected from said target area comprises detecting a prescribed wavelength within said reflected radiant energy, said prescribed wavelength being characteristic of said prescribed color intensity.

3. The method as set forth in claim 2 further including detecting the reflected radiant energy in a plurality of optical channels, determining if the reflected radiant energy in each of said plurality of optical channels contains a respective wavelength, and analyzing the respective wavelengths detected in each optical channel to ascertain whether said prescribed color intensity is present in the reflected radiant energy.

4. The method as set forth in claim 3 further including detecting the intensity of the incident radiant energy from said flashlamp that falls upon said target area, and normalizing the detected reflected radiant energy in each of said plurality of channels as a function of said detected incident radiant energy so as to remove variations in the intensity of the detected reflected radiant energy caused by variations in the intensity of the incident radiant energy.

5. The method as set forth in claim 3 wherein the plurality of optical channels comprises three optical channels, and wherein the wavelength detected in each of said three optical channels corresponds to a color intensity of red, blue and yellow, respectively.

6. The method as set forth in claim 1 further including impinging said ablated material with a particle stream to clean said structure.

7. The method as set forth in claim 6 wherein the reflected radiant energy from the target area corresponds to a trailing edge of the pulse of radiant energy generated by said flashlamp.

8. The method as set forth in claim 6 further including the step of scanning said pulsed radiant energy and said particle stream over said structure at a scan speed.

9. The method as set forth in claim 6 further including the step of scanning said pulsed radiant energy and said particle stream over said structure in incremental steps following a prescribed scan path.

10. The method as set forth in claim 6 wherein the reflected radiant energy from the target area corresponds to radiant energy that is generated by a simmer current applied to said flashlamp.

11. A system for removing a layer of material from a structure, comprising:
   a source of radiant energy that generates pulses of radiant energy having an intensity sufficient to ablate said layer of material;
   means for irradiating a target area on said structure with a series of said pulses of radiant energy for the purpose of ablating said layer of material;
   monitoring means for monitoring radiant energy from said source of radiant energy that is reflected from said target area in order to sense the presence of a prescribed color intensity that is different from a known color intensity of the layer of material being ablated by said irradiating means; and
   feedback means for controlling the irradiation of the target area with said source of radiant energy as a function of the color intensity sensed by said monitoring means.

12. The system as set forth in claim 11 wherein said monitoring means includes photodetection means for detecting a prescribed wavelength within the radiant energy of said source that is reflected from said target area, said prescribed wavelength being characteristic of said prescribed color intensity.

13. The system as set forth in claim 12 wherein said photodetection means further includes:
   a plurality of optical channels, each being adapted to receive a portion of the radiant energy of aid source that is reflected from said target area;
   first detection means for detecting if the reflected radiant energy in each of aid plurality of optical channels contains a respective wavelength; and
   processor means for analyzing the respective wavelengths detected in each optical channel to ascertain whether said prescribed color intensity is present in the reflected radiant energy.

14. The system as set forth in claim 13 wherein said photodetection means further includes second detection means for detecting the intensity of the incident radiant energy generated by said source of radiant energy that falls upon said target area, and wherein said processor means includes means for normalizing the detected reflected radiant energy detected by said first detection means as a function of said detected incident radiant energy detected by said second detection means, whereby any variations in the intensity of the detected reflected radiant energy caused by variations in the intensity of the incident radiant energy may be removed.

15. The system as set forth in claim 11 further including means for impinging said ablated material with a particle stream to clean said structure.

16. The system as set forth in claim 11 wherein said source of radiant energy comprises a flashlamp, and wherein said monitoring means includes means for sampling the reflected radiant energy at a prescribed sampling time relative to the generation of a pulse of radiant energy by said flashlamp.

17. The system as set forth in claim 16 wherein the prescribed sampling time samples the reflected radiant energy at a time coincident with a trailing edge portion of said pulse of radiant energy.

18. The system as set forth in claim 16 wherein the prescribed sampling time samples the reflected radiant energy at a time corresponding to the application of a simmer current to said flashlamp.

* * * * *

UNITED STATES PATENT AND TRADEMARK OFFICE
CERTIFICATE OF CORRECTION

PATENT NO. : 5,281,798

DATED : 1/25/94

INVENTOR(S) : Hamm, et al

It is certified that error appears in the above-identified patent and that said Letters Patent is hereby corrected as shown below:

IN THE CLAIMS: Column 21, line 12, Claim 12, after "energy of", change "aid" to --said--. Column 21, line 15, Claim 15, after "each of", change "aid" to --said--.

Signed and Sealed this

Twenty-eighth Day of June, 1994

Attest:

BRUCE LEHMAN

Attesting Officer Commissioner of Patents and Trademarks